United States Patent [19]

Bradford et al.

[11] Patent Number: Plant 7,502

[45] Date of Patent: Apr. 23, 1991

[54] CHERRY TREE (AARON GEE)

[76] Inventors: Norman G. Bradford, 11875 E. Savana Rd.; Lowell G. Bradford, 12439 E. Savana Rd., both of Le Grand, Calif. 95333

[21] Appl. No.: 459,256

[22] Filed: Dec. 29, 1989

[51] Int. Cl.[5] ..... A01H 5/00

[52] U.S. Cl. ..... Plt./37

[58] Field of Search ..... Plt. 37

[56] References Cited

U.S. PATENT DOCUMENTS

P.P. 6,407 11/1988 Bradford et al. ..... Plt. 37

*Primary Examiner*—James R. Feyrer

[57] ABSTRACT

The present invention relates to a cherry tree and more particularly to a new and distinct variety broadly characterized by a dense, large size, vigorous, very productive tree that produces fruit that is large in size, dark red in color, very attractive cosmetically, resistant to cracking and doubling, and matures in the latter part of May under the ecological conditions prevailing at Le Grand (Merced County), Calif. The tree produces a blossom that is self-sterile, thus requiring cross-pollination by another cherry tree to bear fruit, and the best pollinator determined to date is the Bing Cherry Tree (unpatented). The variety was developed as the result of a second generation seedling from the Bing Cherry Tree.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of cherry tree, which has been denominated varietally as "Aaron Gee". The present invention was hybridized by us in 1982, and the resulting seedling was planted in a cultivated area of our experimental orchard at Bradford Farms near Le Grand, Calif. in Merced County (San Joaquin Valley). Specifically, the seedling was originated by using an unnamed cherry seedling as the selected seed parent and an unnamed cherry seedling as the selected pollen parent. However, the unnamed seed parent was a seedling of an open pollinated Bing Cherry Tree (unpatented), making the present variety a second generation seedling of the Bing.

The instant variety is similar to its grandparent, the Bing Cherry, by being self-sterile and by producing dark red fruit that is crack resistant, but is distinguished from that variety by being larger in size, 3 days earlier in ripening, and less prone to doubling.

The present variety is most similar to the Tulare Cherry (U.S. Plant Pat. No. 6,407) by producing fruit that is dark red in color, resistant to cracking, and not prone to doubling, but is distinguished from that variety by being more vigorous, more productive, and producing fruit that is much larger in size, 5 days later in maturing, and that has a shorter stem.

Subsequent to origination of the present variety of cherry tree, we asexually reproduced it by budding and grafting, and such reproduction of plant and fruit characteristics were true to the original plant in all respects.

DRAWING

The accompanying photograph shows several detached fruits in various positions to exhibit the characteristics of the whole fruit in skin color and form, a characteristic fruit divided on its source plane showing the flesh and stone, a branch with leaves and a bunch of cherries attached, and several detached leaves, all typical of the subject variety.

POMOLOGICAL CHARACTERISTICS

Referring now more specifically to the pomological characteristics of this new and distinct variety of cherry tree, the following has been observed under the ecological conditions prevailing near Le Grand, Merced County (San Joaquin Valley), Calif. All major color code designations are by reference to the Inter-Society Color Council, National Bureau of Standards. Common color names are also used occasionally.

TREE

Size: Large.
Vigor: Vigorous.
Growth: Spreading and dense.
Form: Vase formed.
Hardiness: Hardy.
Production: Very productive.
Bearing: Regular bearer, but not self-fruitful.
Trunk:
- *Size.*—Medium.
- *Texture.*—Medium.
- *Color.*—Dark grayish reddish brown [47. d.gy.rBr].
- *Lenticels.*—Numerous. Color: Moderate reddish brown [43. m.rBr]. Average size: 7/16" [11.1 mm.].

Branches:
- *Size.*—Medium.
- *Texture.*—Medium.
- *Color.*—Newer wood: Brilliant yellow green [116. brill.YG]. Older wood: Grayish reddish brown [46. gy.rBr].
- *Lenticels.*—Numerous, small.

Leaves:
- *Size.*—Medium. Average length: 6" [152.4 mm.]. Average width: 2¾" [69.9 mm.].
- *Thickness.*—Medium.
- *Form.*—Oval.
- *Apex.*—Mucronate.
- *Bcse.*—Rounded to slightly acute.
- *Surface.*—Glabrous.

*Color.*—Dorsal surface: Moderate olive green [125. m.01G]. Ventral surface: Moderate yellow green [120. m.YG].

*Margin.*—Finely serrate.

*Venation.*—Pinnately net veined.

*Petiole.*—Long. Average length: 1⅛" [28.6 mm.]. Average thickness: 1/16" [1.6 mm.]. Color: Moderate yellow green [120. m.YG].

*Glands.*—Numbers: 2 to 4 per leaf. Position: Some oppositely and some alternately positioned on petiole. Size: Large. Form: Reniform. Color: Light olive [106. 1.01].

*Stipules.*—Numerous. Average length: 3/16" [4.8 mm.].

Flower buds:

*Hardiness.*—Half hardy.

*Size.*—Medium.

*Length.*—Medium.

*Form.*—Free.

Flowers:

*Generally.*—Self-sterile, must be cross-pollinated by other cherry trees to produce fruit. At the present the Bing Cherry (unpatented) appears to be a good pollinator.

*Blooming period.*—Medium compared to other cherries.

*Size.*—Medium.

*Color.*—White [263. White].

FRUIT

Maturity when described: Shipping ripe, May 17, 1989.

Date of picking: May 17, 1989.

Size: Uniform, large.

*Average diameter axially.*—1 1/16" [27.0 mm.].

*Average transversely in suture plane.*—15/16" [23.8 mm.].

*Average in the cheek plane.*—1 3/16" [30.2 mm.].

Form: Uniform, symmetrical, and compressed toward the suture.

*Cheek plane form.*—Slightly oblate.

*Longitudinal section form.*—Oval.

*Transverse section through diameter.*—Elliptical.

Suture: An inconspicuous line that extends from the base but discontinues at the apex.

Ventral surface: Rounded.

Stem cavity: Flaring and circular with suture showing on one side only.

*Depth.*—⅛" [3.2 mm.].

*Breadth.*—¼" [6.4 mm.].

Base: Cuneate.

Apex: Rounded.

Pistil Point: An inconspicuous dot slightly depressed within the suture.

Stem:

*Size.*—Small. Average length: 1⅛" [28.6 mm.]. Average width: 1/16" [1.6 mm.].

Skin:

*Thickness.*—Medium.

*Texture.*—Medium.

*Tenacity.*—Tenacious to flesh.

*Amygdalin.*—Wanting.

*Tendency to crack.*—Slight in wet season.

*Color.*—Vivid dark red [17. v.d.R] over the entire surface.

Flesh:

*Color.*—From dark pink [6. d.Pk] near the skin to moderate red [15. m.R] near the stone cavity.

*Amygdalin.*—Moderate.

*Juice.*—Abundant, rich.

*Texture.*—Medium, meaty.

*Fibers.*—Abundant, fine.

*Ripens.*—Evenly.

*Flavor.*—Sweet and slightly acidic when ripe, but can be excessively acidic if picking immaturely.

*Aroma.*—Very slight.

*Eating quality.*—Very good if ripe, but can be poor if picked immaturely.

Stone

Size: Large.

*Length.*—½" [12.7 mm.].

*Width.*—⅜" [9.5 mm.].

*Breadth.*—5/16" [7.9 mm.].

Type: Semi-freestone.

Form: Obovoid.

Base: Slightly oblique.

Apex: Rounded.

Sides: Equal.

Surface: Smooth.

Ridges: Three small ridges along the ventral edge.

Color: Moderate yellowish brown [77. m.yBr].

Thickness of pit wall: 3/32" [2.4 mm.].

Tendency to split: None observed.

Kernel:

*Form.*—Oval.

*Taste.*—Very bitter.

*Viable.*—Yes.

*Average width.*—3/16" [4.8 mm.].

*Average length.*—5/16" [7.9 mm.].

Pellicle color: Moderate yellowish brown [77. m.yBr].

Amygdalin: Abundant.

USE

Market: Fresh market, both local and long distance shipping.

Keeping quality: Medium.

Shipping quality: Medium.

Resistance to insects: No unusual susceptibilities noted.

Resistance to diseases: No unusual susceptibilities noted.

Resistance to cracking: Good.

Resistance to doubling: Good.

Although the new variety of cherry tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of cherry tree, substantially as illustrated and described, that is similar to its grandparent, the Bing Cherry (unpatented), by being self-sterile and by producing dark red fruit that is crack resistant, but is distinguished therefrom and an improvement thereon by producing fruit that is larger in size, 3 days earlier in ripening, and less prone to doubling, and that is also similar to the Tulare Cherry (U.S. Plant Pat. No. 6,407) by producing fruit that is dark red in color, resistant to cracking and doubling, but is distinguished therefrom and an improvement thereon by being more vigorous, more productive, and producing fruit that is much larger in size, 5 days later in maturing, and that has a shorter stem.

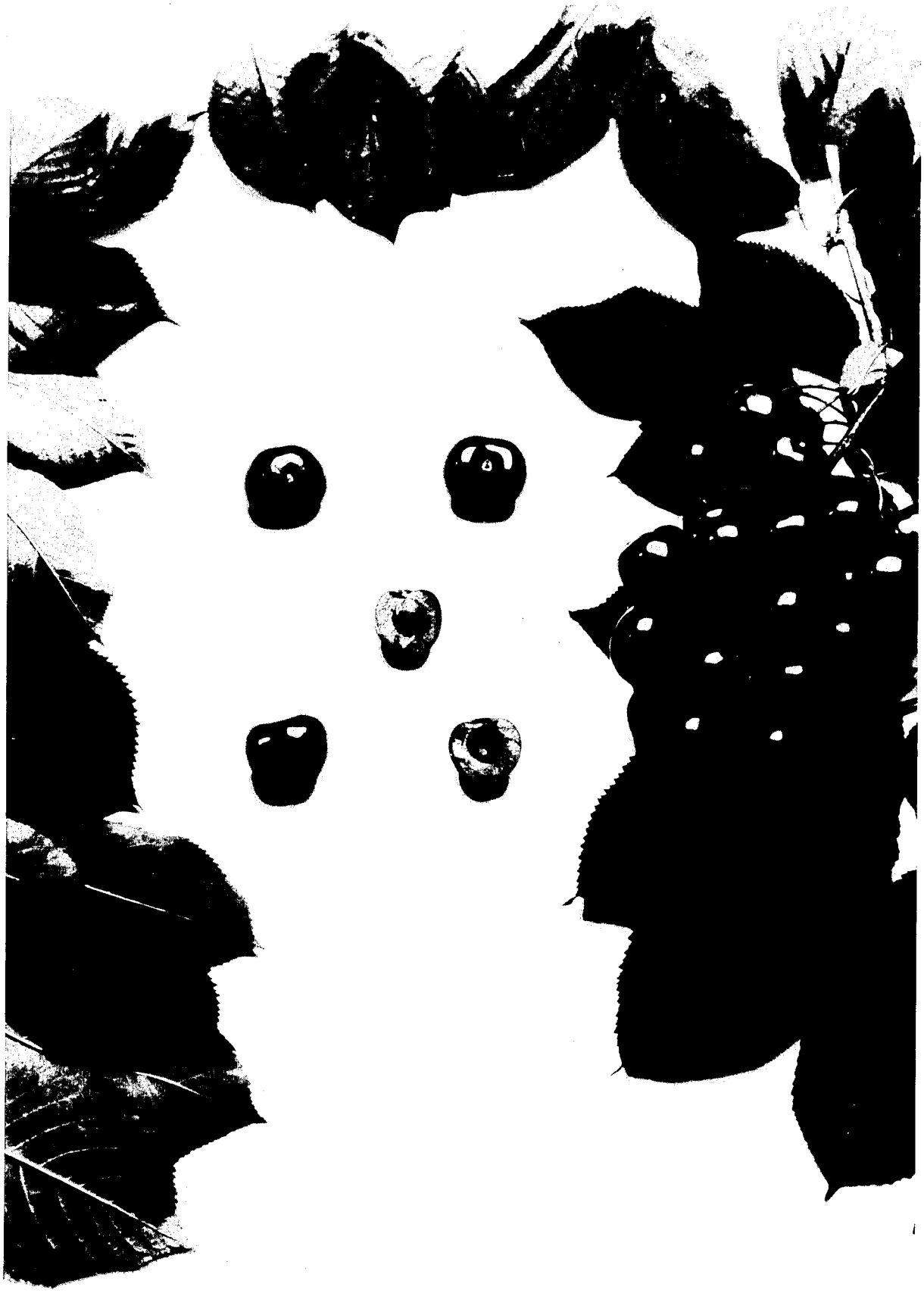

* * * * *